United States Patent [19]

Teetz et al.

[11] Patent Number: 4,558,064

[45] Date of Patent: Dec. 10, 1985

[54] 2-AZASPIRO[4.(3+n)]-3-CARBOXYLIC ACID DERIVATIVES, A PROCESS FOR THEIR PREPARATION, AGENTS CONTAINING THESE DERIVATIVES AND THEIR USE

[75] Inventors: Volker Teetz, Hofheim; Hansjörg Urbach, Kronberg; Reinhard Becker, Wiesbaden, all of Fed. Rep. of Germany

[73] Assignee: Hoechst Aktiengesellschaft, Fed. Rep. of Germany

[21] Appl. No.: 478,780

[22] Filed: Mar. 25, 1983

[30] Foreign Application Priority Data

Mar. 27, 1982 [DE] Fed. Rep. of Germany ....... 3211397

[51] Int. Cl.[4] .................. C07D 209/96; A61K 31/395
[52] U.S. Cl. ..................................... 514/409; 548/408
[58] Field of Search ......................... 548/408; 514/409

[56] References Cited

FOREIGN PATENT DOCUMENTS 50800  5/1952  European Pat. Off. .
12401  6/1980  European Pat. Off. .
37231  7/1981  European Pat. Off. .
94633 11/1983  European Pat. Off. .

OTHER PUBLICATIONS

Schroeder & Lubke, *The Peptides* vol. 1 (pp. IX, XIII--XXIV, 1, 2, 72–75, 246–270) (1965).
Eberle *Perspectives in Peptide Chemistry*, NY, 1981 (pp. 143–155).
Sybertz et al., Chem. Abs. 99, 82251p (1983).

*Primary Examiner*—Mark L. Berch
*Attorney, Agent, or Firm*—Finnegan, Henderson, Farabow, Garrett & Dunner

[57] ABSTRACT

The invention relates to compounds of the formula I

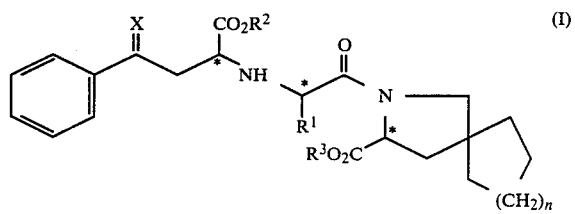

in which n denotes 1, 2, 3 or 4, R is alkyl, alkenyl cycloalkyl, aryl, optionally mono-, di- oder trisubstituted by alkyl, alkoxy, hydroxy, halogen, nitro, amino, alkylamino, dialkylamino or methylenedioxy, or indol-3-yl, $R^1$ denotes an optionally protected radical of a naturally occurring amino acid HOOC—CH(NH$_2$)—$R^1$, $R^2$ denotes hydrogen, alkyl or optionally nitro-substituted aralkyl, $R^3$ denotes hydrogen, alkyl or cycloalkyl or optionally nitro-substituted aralkyl and X denotes 2 hydrogen atoms or 1 oxygen atom, their physiologically tolerated salts with acids and, if $R^2$ and/or $R^3$ denote hydrogen, with bases, a process for their preparation, agents containing these derivatives and their use as medicaments.

9 Claims, No Drawings

2-AZASPIRO[4.(3+n)]-3-CARBOXYLIC ACID DERIVATIVES, A PROCESS FOR THEIR PREPARATION, AGENTS CONTAINING THESE DERIVATIVES AND THEIR USE

The invention relates to compounds of the formula I

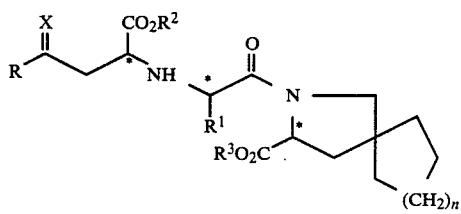

in which
n denotes 1, 2, 3 or 4;
R denotes $(C_1-C_6)$-alkyl, $(C_2-C_6)$-alkenyl, $(C_5-C_9)$-cycloalkyl, $(C_6-C_{12})$-aryl, preferably phenyl, optionally mono-, di- or trisubstituted by $(C_1-C_4)$-alkyl, $(C_1-C_4)$-alkoxy, hydroxy, halogen, nitro, amino, $(C_1-C_4)$-alkylamino, di-$(C_1-C_4)$-alkylamino or methylenedioxy, or indol-3-yl,
$R^1$ denotes a radical of an optionally protected, naturally occuring amino acid HOOC—CH(NH$_2$)—$R^1$,
$R^2$ denotes hydrogen, alkyl having 1 to 6 C atoms or optionally nitro-substituted aralkyl having 7 to 9 C atoms
$R^3$ denotes hydrogen, alkyl having 1 to 10 C atoms, cycloalkyl having 3 to 10 C atoms or optionally nitro-substituted aralkyl having 7 to 9 C atoms and
X denotes 2 hydrogen atoms or 1 oxygen atom,
and their physiologically tolerated salts with acids and, if $R^2$ and/or $R^3$ denote hydrogen, with bases.

$R^1$ may for example be the optionally protected side chain of Ala, Ser, Thr, Val, Leu, Ile, Asp, Asp-NH$_2$, Glu, Glu-NH$_2$, Cys, Met, Arg, Lys, Hyl, Orn, Cit, Tyr, Phe, Trp, and His.

In the case where $R^1$ is a side chain of a protected alpha-amino acid, for example protected Ser, Thr, Asp, Asn, Glu, Gln, Arg, Lys, Hyl, (δ-Hydroxylysine), Cys, (Cysteine), Orn, Cit, (Citrulline), Tyr, Trp, His or Hyp, the groups customary in peptide chemistry are preferred as protecting groups (see Houben-Weyl, vol. XV/1 and XV(2)). In the case where $R^1$ is the protected lysine side chain, the known amino protecting groups, especially $(C_1-C_6)$-alkanoyl, are preferred. Preferred O-alkyl protecting group for Tyr is methyl or ethyl.

In formula I, the C atom in position 3 of the spirocycle and the C atoms marked with an asterisk (*) in the chain can have both the R and the S configuration. However, compounds in which the C atom in position 3 of the spirocycle and in which the C atoms marked with an asterisk in the chain each have the S configuration are preferred.

Those compounds of the formula I are particularly preferred in which n and X have the abovementioned meaning and
$R^1$ denotes methyl, specially 4-methoxybenzyl or 4-ethoxybenzyl,
$R^2$ denotes hydrogen, alkyl having 1 to 4 C atoms, benzyl or nitrobenzyl and
$R^3$ denotes hydrogen.

Furthermore, the invention relates to a process for the preparation of compounds of the formula I, which comprises condensing compounds of the formula II

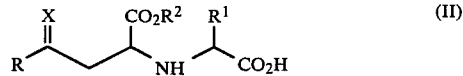

in which R, $R^1$, $R^2$ and X have the abovementioned meanings, with compounds of the formula III

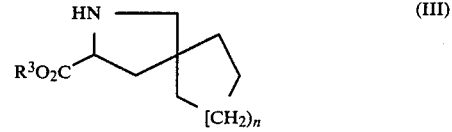

in which $R^3$ has the abovementioned meaning, with the exception of hydrogen, and n represents a whole number from 1 to 4, and then optionally splitting off the radicals $R^2$ and/or $R^3$ by hydrogenolysis, or with added acid or base, and optionally converting the compounds of the formula I obtained into their physiologically tolerated salts.

The condensation of the compounds of the formula II with the esters of the formula III is preferably carried out by known processes of peptide chemistry. Those processes are particularly preferred which provide adequate protection from racemization, such as, for example, the DCC/HOBt method or the alkanephosphonic anhydride method described in German Offenlegungsschrift 2,901,843. Examples of suitable radicals $R^3$ in the abovementioned esters are groups which can be split off by hydrogenolysis (cf. for example Org. Reactions I (1953) 273), preferably benzyl or nitrobenzyl, or groups which can be split off by acid or base (cf. for example Houben-Weyl, Volume 8 (1952)) preferably tert.butyl.

Compounds of the formula I, in which at least one of the radicals $R^2$ and $R^3$ is hydrogen, can be converted by known methods into the esters of the formula I, in which $R^2$ and $R^3$ have the abovementioned meaning with the exception of hydrogen.

Processes for the preparation of compounds of the formula II have already been proposed.

The invention further relates to a process for the preparation of compounds of the formula III in which n denotes 1, 2, 3 and 4 and $R^3$ denotes hydrogen, alkyl or cycloalkyl having 1 to 10 C atoms or optionally nitro-substituted aralkyl having 7 to 9 C atoms, which comprises metalizing compounds of the formula IV

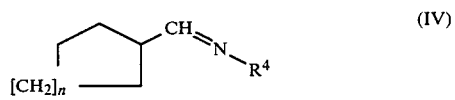

in which n has the abovementioned meaning and $R^4$ represents alkyl having 1 to 6 C atoms, with an organometallic reagent in an inert solvent and then reacting with compounds of the formula V

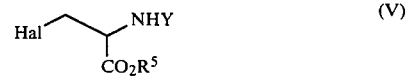

in which Hal denotes bromine or chlorine, $R^5$ denotes alkyl having 1 to 6 C atoms or aralkyl having 7 to 9 C atoms and Y denotes an aliphatic or aromatic acyl radical which can be split off by acid, or reacting with compounds of the formula VI

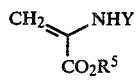
(VI)

in which $R^5$ and Y have the abovementioned meaning, to give the compounds of the formula VII

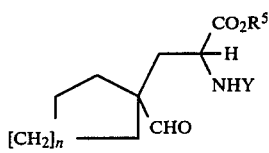
(VII)

in which n, $R^5$ and Y have the abovementioned meaning, cyclizing the latter by acid treatment to give compounds of the formula VIII

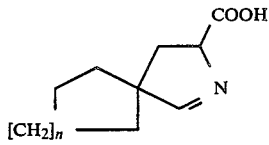
(VIII)

in which n has the abovementioned meaning, reducing the latter to give compounds of the formula III in which n has the abovementioned meaning and $R^3$ represents hydrogen, and then esterifying the latter to give compounds of the formula III in which n has the abovementioned meaning and $R^3$ has the abovementioned meaning with the exception of hydrogen.

The Schiff's bases (formula IV) of an alkylamine $R^4$—$NH_2$, such as, for example, butylamine, and an appropriate cycloalkanealdehyde having 5 to 8 ring C atoms, are converted into their carbanions with an organometallic compound in an inert solvent such as, for example, diethyl ether, THF or dimethoxyethane.

In respect of the N-acylated halogenoserine esters of the formula Y or the corresponding acrylates of the formula VI, Y is preferably an acyl radical which can be split off by acid, for example acetyl or tert.-butyloxycarbonyl and $R^5$ preferably denotes methyl, but also another alkyl or aralkyl.

The compounds of the formula VII are obtained as racemates. They are cyclized in acids, preferably aqueous mineral acids, such as, for example, 2N hydrochloric acid, with simultaneous deacylation and ester cleavage to give compounds of the formula VII.

The reduction of the compounds of the formula VII can be carried out either by catalytic hydrogenation (for example on Pt/C under standard conditions) or with complex borohydrides or borane-amine complexes, preferably in lower alcohols.

The aminoacids of the formula III are converted into the corresponding esters by methods known per se (cf. for example Houben-Weyl, Volume 8 [1952] pages 359–680).

They are obtained as salts of mineral acids or other strong acids, for example toluenesulfonats, and can be employed as such or in the form of the free bases in the subsequent peptide coupling. No special protection of the iminonitrogen in compounds of the formula II is necessary in this process.

Diesters of the formula I are obtained, from which the monoesters or dicarboxylic acids according to formula I can be prepared, depending on the selected combination of esters, by acidic, basic and/or hydrogenolytic methods (in the case where X=oxygen, for example, on Pd/BaSO$_4$ in DMF). Separation of the diastereomers produced is possible both with the diesters of the formula I and also with the monoesters or dicarboxylic acids of the formula I by chromatographic processes, for example, column chromatography on silica gel. In particular cases, fractional crystallization of the compounds, mostly in the form of their salts with mineral acids (for example their hydrochlorides), is possible, to give pure diastereomeric products.

The invention also relates to compounds of the formula IX

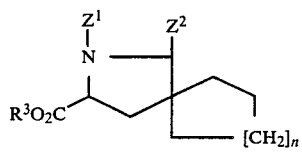
(IX)

in which
n has the abovementioned meaning, $Z^1$ and $Z^2$ each denote hydrogen or, together, denote a chemical bond and
$R^3$ denotes hydrogen, alkyl or cycloalkyl having 1 to 10 C atoms, preferably n-butyl or optionally nitro-substituted aralkyl having 7 to 9 C atoms.

The new compounds of the general formula I have a long-lasting and powerful hypotensive effect. They are well absorbed after oral administration and can be employed for controlling high blood pressure of various etiologies and can be used alone or combined with other compounds having hypotensive, vasodilator or diuretic activities. Administration can be intravenously, subcutaneously or orally, oral administration being preferred. The dosage on oral administration is 0.1–100 mg, preferably 1–50 mg, especially 1–30 mg for an adult person having normal weight. This corresponds to a dose of 1–1,300 mg/kg/day, preferably 13–700 mg/kg/day, especially 13–400 mg/kg/day.

It can also be increased in severe cases, since toxic properties have not hitherto been observed. It is also possible to decrease the dose and this is particularly appropriate when diuretics are administered concurrently. On intravenous or subcutaneous administration, the single dose should be between 0.01 and 20 mg.

In animal experiments, the following effects, for example, were obtained: the suppression of the pressor response in the rat induced by 310 ng of angiotensin I was measured.

(a) i.v. administration (30 minutes after administration)

| | | | | Compound I | | | |
|---|---|---|---|---|---|---|---|
| R | $R^1$ | $R^2$ | $R^3$ | n | X | Dose | % inhibition |
| $C_6H_5$ | $CH_3$ | $C_2H_5$; | H | 1; | = $H_2$ | 100 µg/kg | 95% |
| $C_6H_5$ | $CH_3$ | $C_2H_5$; | H | 2; | = $H_2$ | 100 µg/kg | 95% |
| $C_6H_5$ | $CH_3$ | $C_2H_5$; | H | 2; | = O | 100 µg/kg | 95% |
| $C_6H_5$ | $CH_3$ | H; | H | 3; | = $H_2$ | 100 µg/kg | 95% |

(b) i.d. administration (30 minutes after administration)

| R | R¹ | R² | R³ | n | X | Dose | % inhibition |
|---|---|---|---|---|---|---|---|
| $C_6H_5$ | $CH_3$ | $C_2H_5$ | H | 1; | = $H_2$ | 1 mg/kg | 85–95% |
| $C_6H_5$ | $CH_3$ | $C_2H_5$ | H | 2; | = $H_2$ | 0.1 mg | 60–70% |

The compounds of the formula I with $R^3$=hydrogen are present in the form of internal salts. If both carboxyl groups are free, alkali metal and calcium, magnesium and zinc salts and salts with physiologically acceptable amines can also be formed. Furthermore, the free amino group can be reacted with a mineral acid, such as HCl, HBr, $H_3PO_4$, $H_2SO_4$, or organic acid, such as citric, tartaric, maleic, fumaric acid, to give a salt.

The following examples are intended to illustrate the procedures according to the invention but without restricting the invention to the substances mentioned here as being representative. Satisfactory analyses (CHN analyses, NMR spectra) were obtained for all compounds, including those not mentioned in the examples.

EXAMPLE 1

2-Azaspiro[4.5]decane-3-carboxylic acid 6.4 g of butyllithium (in the form of a hexane solution) were added to 16.7 g of butyliminomethylcyclohexane in 300 ml of anhydrous dimethoxyethane at −76° C. under protective gas (argon). 15 min. after completion of addition, 18 g of N-acetylchloroserine methyl ester in 100 ml of DME were added dropwise, with efficient cooling. The mixture was stirred for a further 1 hour at a low temperature, allowed to warm up and evaporated to a small volume in vacuo. The crude mixture was acidified with 200 ml of 2N HCl and heated to reflux for 45 min. The mixture was evaporated in vacuo, the residue was taken up in glacial acetic acid, 1 g of Pt/C (10% Pt) was added and hydrogenation was carried out under normal pressure. The mixture was filtered, evaporated and chromatographed over a silica gel column with the system chloroform/methanol/glacial acetic acid/water 25:15:2:2. The amino acid crystallized from the appropriate eluate after evaporation.

Melting point 205° C. (decomposition).

Rf: 0.51 (silica gel plates, system as for column chromatography).

EXAMPLE 2

(S,S,S)-N-(1-Carboethoxy-5-phenylpropyl)alanyl-2-azaspiro[4.4]nonane-3-carboxylic acid 14.8 g of benzyl (D,L)-2-azaspiro[4.4-nonane-3-carboxylate hydrochloride, 6.7 g of 1-hydroxybenzotriazole and 13.8 g of (S,S)-N-(1-carboethoxy-3-phenylpropyl)alanine were dissolved in 200 ml of DMF and brought to reaction overnight with 10.2 g of dicyclohexylcarbodiimide. The addition of tertiary bases, for example 6.4 ml of N-ethylmorpholine, increases the yield only insignificantly. The precipitated DC-urea was removed by filtration, the filtrate was evaporated in vacuo, the residue was taken up in ethyl acetate, extracted by shaking with aqueous sodium bicarbonate solution and the organic phase was dried over solid sodium sulfate and again evaporated. The residue was separated by column chromatography on 1 kg of silica gel (pore size 60 Å) with the system ethyl acetate/petroleum ether 2:1. The (S,S,S) isomer was initially eluted, followed by the (S,S,R) isomer. Thin layer chromatography on silica gel plates in the above mobile phase: Rf=0.7 and 0.6 respectively. After evaporation of the appropriate eluates, the compounds were obtained as viscous oils. The NMR spectra (in $CDCL_3$) confirm the structure.

EXAMPLE 3

(S,S,S)- and (S,S,R)-N-(1-Carboethoxy-3-phenylpropyl)alanyl-2-azaspiro[4.4]nonane-3-carboxylic acid The diastereomeric benzyl esters obtained in Example 2 were taken up in 200 ml of methanol and the benzyl groups were removed by hydrogenolysis with 1 g of Pd/C (10% Pd). After completion of uptake of hydrogen, the mixture was filtered and the filtrate was evaporated in vacuo. On adding pentane, a solid hygroscopic foam of the zwitterionic dipeptide derivatives could be obtained on evaporating in vacuo.

S,S,S-compound: $[\alpha]_D^{20} = -78.9$ (c=1.5, methanol)
S,S,R-compound: $[\alpha]_D^{20} = +28.4$ (c=1, methanol)

The corresponding 2-azaspiro[4.5]-, [4,6]- and [4.7]alkane-3-carboxylic acid derivatives were obtained in an analogous manner. The optical rotations for the (S,S,S)- and (S,S,R)-N-(1-carboethoxy-3-phenylpropyl)alanyl-2-azaspiro[4.5]decane-3-carboxylic acid were, for example, (S,S,S)-compound: $[\alpha]_D^{21} = -38.3$ (c=1, methanol)
(S,S,R)-compound: $[\alpha]_D^{21} = +18.5$ (c=1, methanol)

EXAMPLE 4

N-(1-Carboethoxy-3-oxo-3-phenylpropyl)alanyl-2-azaspiro[4.5]decane-3-carboxylic acid The compound can be obtained by various routes:
(a) In analogy to Examples 2 and 3. The cleavage of the benzyl ester is advantageously carried out with Pd/BaSO₄ in DMF, in order to prevent an undesired reduction of the keto group α to the phenyl ring. The hydrogenation is stopped after completion of the rapid benzyl ester cleavage.
(b) Using tert.-butyl 2-azaspiro[4.5]decane-3-carboxylate for peptide coupling and subsequent acidic ester cleavage with HCl/dioxane or anhydrous trifluoroacetic acid, in accordance with known methods in peptide chemistry.

EXAMPLE 3

N-(2-Carboxy-3-phenylpropyl)alanyl-2-azaspiro[4.5]-decane-3-carboxylic acid 1 g of the ethyl ester from Example 3 was taken up in 25 ml of dioxane and hydrolyzed with an equivalent amount of 2N sodium hydroxide solution. The pH was adjusted to 4 with a little hydrochloric acid, the solution was evaporated to dryness, a little saturated NaCl solution was added and the title compound was extracted with n-butanol.

Yield: 700 mg.

Rf: 0.31 (silica gel, system: $CHCl_3$/methanol/glacial acetic acid 50:10:2).

EXAMPLE 6

General procedure for the synthesis of the spiro-amino-acid benzyl ester hydrochlorides 50 g of thionyl chloride are added dropwise to 300 ml of benzyl alcohol at −5° C. The mixture is stirred a further 30 min. and then 0.2 mole of aminoacid hydrochloride is added. The reaction is complete after 6–10 hours at room temperature. The reaction solution is evaporated in vacuo and the residue is precipitated with diisopropyl ether. In this manner, benzyl 2-azaspiro[4.5]decane-3-carboxylate hydrochloride, for example, was obtained:

Melting point 145° C., Rf=0.71 (silica gel, system: CHCl$_3$/CH$_3$OH/CH$_3$COOH 50:10:2).

We claim:

1. A compound of the formula I

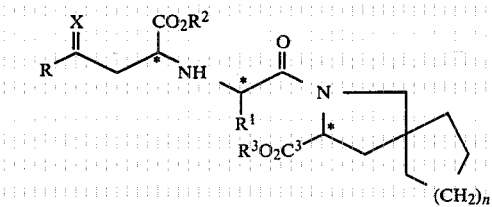

in which n denotes 1, 2, 3 or 4,

R denotes (C$_1$–C$_6$)-alkyl, (C$_2$–C$_6$)-alkenyl, (C$_5$–C$_9$)-cycloalkyl, (C$_6$–C$_{12}$)-aryl, optionally mono-, di- or trisubstituted by (C$_1$–C$_4$)-alkyl, (C$_1$–C$_4$)-alkoxy, hydroxy, halogen, nitro, amino, (C$_1$–C$_4$)-alkylamino, di-(C$_1$–C$_4$)-alkylamino or methylenedioxy or indol-3-yl, R$^1$ denotes a side-chain of an amino acid selected from the group consisting of Ala, Ser, Thr, Val, Leu, Ile, Asp, Asp-NH2, Glu, Glu-NH2, Cys, Met, Arg, Lys, Hyl, Orn, Cit, Tyr, Phe, Trp and His, a side chain of Lys, Hyl or Orn, the amino group of which is protected by (C$_1$–C$_6$)-alkanoyl, or Ser, Thr, Hyl or Tyr, the hydroxyl group of which is protected by alkyl, R$^2$ denotes hydrogen, alkyl having 1 to 6 C atoms or optionally nitro-substituted aralkyl having 7 to 9 C atoms, R$^3$ denotes hydrogen, alkyl having 1 to 10 C atoms, cycloalkyl having 3 to 10 C atoms or optionally nitro-substituted aralkyl having 7 to 9 C atoms and X denotes 2 hydrogen atoms or 1 oxygen atom, and its physiologically tolerated salts with acids and, if R$^2$ and/or R$^3$ denote hydrogen, with bases.

2. A compound of the formula I as claimed in claim 1, wherein the C atom in the 3-position of the spirocycle and the C atoms marked with an asterisk in the chain each have the S configuration.

3. A compound of the formula I as claimed in claim 1, wherein

R$^1$ denotes methyl, 4-methoxybenzyl or 4-ethoxybenzyl,

R$^2$ denotes hydrogen, an alkyl having 1 to 4 C atoms, benzyl or nitrobenzyl and R$^3$ denotes hydrogen.

4. A compound of the formula I as claimed in claim 1, wherein n denotes 2, R$^1$ denotes 4-methoxybenzyl or 4-ethoxybenzyl.

5. A pharmaceutical composition comprising (1) a hypotensively effective amount of a compound as claimed in claim 1 or a pharmaceutically acceptable salt thereof; and (2) a pharmaceutically acceptable carrier.

6. A method of treating hypertension by administering to a patient a compound as claimed in claim 1 or a pharmaceutically acceptable salt thereof in an amount effective to achieve a hypotensive effect in said patient.

7. A compound of the formula I as claimed in claim 1 in which n denotes 1, 2, 3, or 4, R denotes phenyl, R$^1$ denotes an alkyl residue of a naturally occurring amino acid of the formula HOOC—CH(NH$_2$)—R$^1$, R$^2$ denotes hydrogen, an alkyl having 1 to 6 C atoms or an optionally nitro-substituted aralkyl having 7 to 9 C atoms, R$^3$ denotes hydrogen, an alkyl having 1 to 10 C atoms, a cycloalkyl having 3 to 10 C atoms or an optionally nitro-substituted aralkyl having 7 to 9 C atoms and X denotes 2 hydrogen atoms or 1 oxygen atom, and its physiologically tolerated salts with acids and, if R$^2$ and/or R$^3$ denote hydrogen, with bases.

8. A compound of claim 7, wherein X denotes an oxygen atom.

9. A compound of claim 1, wherein X denotes an oxygen atom.

* * * * *

UNITED STATES PATENT AND TRADEMARK OFFICE
CERTIFICATE OF CORRECTION

PATENT NO. : No. 4,558,064
DATED : December 10, 1985
INVENTOR(S) : Volker Teetz, Hansjorg Urbach and Reinhard Becker It is certified that error appears in the above-identified patent and that said Letters Patent is hereby corrected as shown below:

In the Title:

In the first line, change "2-Azasfiro[4.(3+n)]-3-Carboxylic Acid" to:
--2-Azaspiro[4.(3+n)]-3-Carboxylic Acid--.

Signed and Sealed this

Eighth Day of April 1986

[SEAL]

Attest:

DONALD J. QUIGG

Attesting Officer

Commissioner of Patents and Trademarks